(12) United States Patent
Moriyama et al.

(10) Patent No.: US 7,014,851 B2
(45) Date of Patent: Mar. 21, 2006

(54) PROCESS FOR INHIBITING PLATELET AGGREGATION

(75) Inventors: Hiroyoshi Moriyama, Tokyo (JP); Shinsaku Takaoka, Kyoto (JP)

(73) Assignees: V-Tec Co., Ltd., (JP); Japan Bio Science Laboratory Co., Ltd., (JP)

( * ) Notice: Subject to any disclaimer, the term of this patent is extended or adjusted under 35 U.S.C. 154(b) by 0 days.

(21) Appl. No.: 10/932,806

(22) Filed: Sep. 2, 2004

(65) Prior Publication Data

US 2005/0025759 A1 Feb. 3, 2005

Related U.S. Application Data

(62) Division of application No. 10/465,193, filed on Jun. 19, 2003, now abandoned.

(30) Foreign Application Priority Data

Aug. 30, 2002 (JP) .............................. 2002-253030

(51) Int. Cl.
*A61K 38/45* (2006.01)
*A61K 38/48* (2006.01)
*A23L 1/30* (2006.01)

(52) U.S. Cl. ............... 424/94.5; 435/71.1; 435/183; 435/252.1; 435/252.31; 424/780; 426/72

(58) Field of Classification Search ........... 424/94.5, 424/71.1, 780; 426/72; 435/183, 253.31, 435/71.1, 252.1, 252.31, 72
See application file for complete search history.

(56) References Cited

U.S. PATENT DOCUMENTS

| | | | | |
|---|---|---|---|---|
| 5,139,871 A | * | 8/1992 | Wallace et al. | 428/368 |
| 5,760,042 A | * | 6/1998 | Kaneko et al. | 514/263.24 |
| 5,914,242 A | * | 6/1999 | Honkanen et al. | 435/7.71 |
| 5,977,160 A | * | 11/1999 | Pfeffer et al. | 514/424 |
| 6,071,968 A | * | 6/2000 | Nishino et al. | 514/617 |
| 2001/0046697 A1 | | 11/2001 | Takaoka | |
| 2004/0223962 A1 | * | 11/2004 | Riordan | 424/94.63 |

FOREIGN PATENT DOCUMENTS

JP 299277 10/2001

OTHER PUBLICATIONS

Shinsaku Takaoka: Japan Food Science, 39 (9), pp. 55-60, 2000.

* cited by examiner

*Primary Examiner*—Herbert J. Lilling
(74) *Attorney, Agent, or Firm*—Price, Heneveld, Cooper, DeWitt & Litton, LLP

(57) ABSTRACT

An object of the present invention is to provide a platelet aggregation inhibitor without side effects and a supplement food effective for inhibiting platelet aggregation. The platelet aggregation inhibitor has nattokinase as an active ingredient and has *Bacillus* natto culture extract, containing a high proportion of nattokinase containing 1 μg/g or less of vitamin $K_2$ on a dry weight basis, as an active ingredient. The supplement food effective for inhibiting platelet aggregation has nattokinase as an active ingredient and has *Bacillus* natto culture extract, containing a high proportion of nattokinase containing 1 μg/g or less of vitamin $K_2$ on a dry weight basis, as an active ingredient.

6 Claims, 4 Drawing Sheets

PROCESS FOR INHIBITING PLATELET AGGREGATION

CROSS-REFERENCE TO RELATED APPLICATION

This application is a divisional of U.S. application Ser. No. 10/465,193 entitled PLATELET AGREGATION INHIBITOR AND SUPPLEMENT FOOD EFFECTIVE FOR INHIBITING PLATELET AGGREGATION, filed Jun. 19, 2003 now abandoned, the entire disclosure of which is incorporated herein by reference.

BACKGROUND OF THE INVENTION

1. Field of the Invention

The present invention relates to the use of a platelet aggregation inhibitor and, more particularly, to a platelet aggregation inhibitor whose active ingredient is nattokinase and a supplement food using the same.

2. Description of the Related Art

Previously, nattokinase has been known as a thrombolytic enzyme, and a thrombolytic activity of the nattokinase has been known to be excellent not only for preventing thrombosis but also for treating the thrombosis (Shinsaku Takaoka: Japan Food Science, 39 (9), 55–60, 2000).

The nattokinase is not contained in soybeans, but produced in the course of fermentation when *Bacillus* natto acts on the soybeans, and further, the nattokinase also contains vitamin $K_2$ as a blood coagulation factor. Therefore, ingestion of natto or *Bacillus* natto culture extract which contains the nattokinase as a thrombolytic enzyme, for the purpose of preventing thrombosis, means that the vitamin $K_2$ is also ingested simultaneously. Thus, there has been a problem that an effect of the vitamin K-dependent coagulation factor synthesis inhibitor is counteracted. Consequently, a technique for producing *Bacillus* natto culture extract whose vitamin $K_2$ content is 1 µg/g or less on a dry weight basis has been developed (see Japanese Patent Laid-Open No. 2001-299277).

SUMMARY OF THE INVENTION

As a result of making an intensive study on effective actions of nattokinase on human bodies in addition to thrombolytic action thereof, the inventors have now found that the nattokinase has inhibitory action on platelet aggregation. As an example of a platelet aggregation inhibitor which has practically been used as an anti-platelet agent clinically, aspirin or ticlopidine for example is orally administered. However, these agents produce side effects. For example, side effects such as gastrointestinal injury and aspirin-induced asthma are produced if the aspirin is administered, whereas side effects such as thrombocytopenic purpura (TTP), agranulocytosis, and serious hepatopathy are produced if the ticlopidine is administered.

Therefore, an object of the present invention is to provide a platelet aggregation inhibitor without side effects and a supplement food effective for inhibiting platelet aggregation.

To achieve the above described object, a platelet aggregation inhibitor according to the present invention is intended to have nattokinase as an active ingredient and to have *Bacillus* natto culture extract, containing a high proportion of nattokinase containing 1 µg/g or less of vitamin $K_2$ on a dry weight basis, as an active ingredient.

In addition, a supplement food effective for inhibiting platelet aggregation according to the present invention is intended to have nattokinase as a principal ingredient and to have *Bacillus* natto culture extract, containing a high proportion of nattokinase containing 1 µg/g or less of vitamin $K_2$ on a dry weight basis, as a principal ingredient.

The nattokinase has been ingested by eating natto since hundreds years before, so that its safety has empirically been proven. Also, in the case of nattokinase contained in the *Bacillus* natto culture extract (of powder type), it has been observed that the nattokinase does not affect general conditions of mouse at all in an acute toxicity test. In this case, an $LD_{50}$ value was considered to be 2,000 mg/kg or more. Further, it has also been demonstrated that results from a reverse mutation test are negative (Shinsaku Takaoka: Japan Food Science, 39 (9), 55–60, 2000).

When a vitamin $K_2$ content in the nattokinase is 1 µg/g or less on a dry weight basis, the above described disorders caused by the vitamin $K_2$ are not produced. The nattokinase, which has been proved to be safe as described above, is available not only for agents but also for foods (supplement foods).

According to the present invention, it is possible to provide a platelet aggregation inhibitor which does not cause problems such as side effects and to provide a supplement food which is safe and effective for inhibiting platelet aggregation. According to the present invention, it is also possible to treat and prevent myocardial infarction or brain infarction, because blood clots are hardly formed inside a blood vessel and growth of the blood clots is also inhibited.

These and other features, advantages and objects of the present invention will be further understood and appreciated by those skilled in the art by reference to the following specification, claims and appended drawings.

DETAILED DESCRIPTION OF THE PREFERRED EMBODIMENTS

Figure 1:
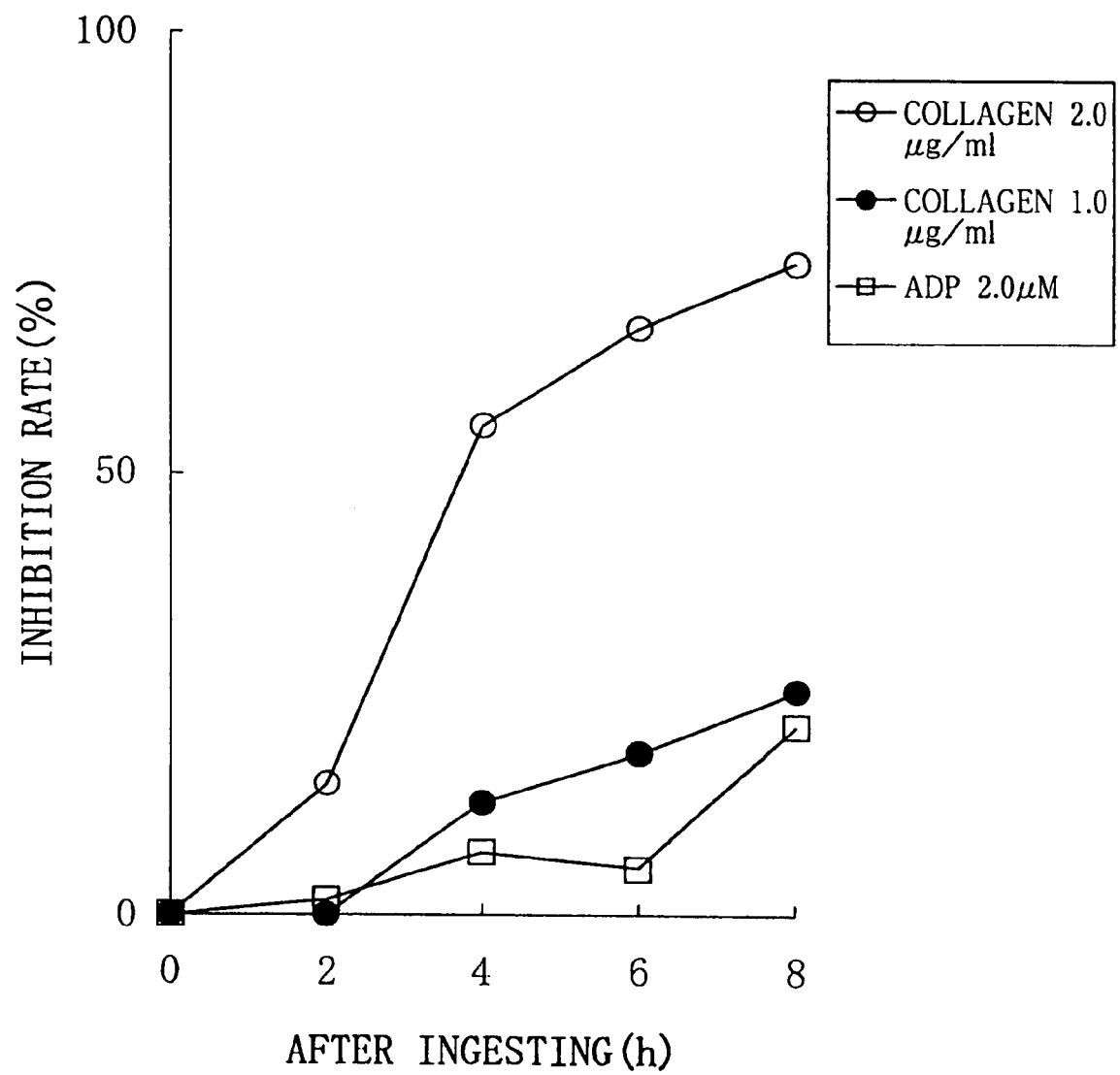
FIG. 1 is a diagram showing a change of a platelet inhibition rate with respect to time after the ingestion of nattokinase, when using collagen and ADP as inducers.

Examples of producing an extract and processing the extract and examples of the present invention will be described below.

An example of producing *Bacillus* natto culture extract containing a high proportion of nattokinase whose vitamin $K_2$ content is 1 µg/g or less on a dry weight basis is as follows.

PRODUCTION EXAMPLE

Bacillus natto is taken into a liquid medium which contains soybeans as principal materials and is cultured to produce a culture solution containing a high proportion of nattokinase. Then the Bacillus natto and the vitamin $K_2$ are removed by coagulation sedimentation filtration using a chitosan solution. The obtained culture solution, which has been subjected to sterile filtration through a membrane filter, is dried and processed into powder.

PROCESSING EXAMPLE

The above described Bacillus natto culture extract can be processed into a certain form such as a capsule, a tablet, a drinkable preparation, a granule, or paste. Examples of processing the culture extract will be described below.

When the above described culture extract is processed into a soft capsule form for example, 36.7 mg of Bacillus natto culture extract powder (20000 FU/g), 10 mg of soybean lecithin, 133.3 mg of soybean oil, 15 mg of beewax, and 15 mg of glycerin fatty acid ester are mixed and emulsified to obtain 210 mg in total of an emulsified mixture, and then the emulsified mixture is filled into a film cell made of 130 mg in total of a material composed of 100 mg of gelatin and 30 mg of glycerin. Consequently, a soft capsule having a total weight of 340 mg is formed. Administration of 3 to 6 capsules thus formed per day is equivalent to ingestion of nattokinase contained in 1 or 2 packs (50 to 100 g) of natto on the market.

Similarly, when a hard capsule is formed, 36.7 mg of Bacillus natto culture extract powder (20000 FU/g), 209.8 mg of dextrin, and 13.5 mg of sucrose fatty acid ester are mixed to obtain 260 mg in total of a mixture, and then the mixture is filled into a gelatin hard capsule (70 mg) to make a No. 2 gelatin hard capsule having a total weight of 330 mg. Administration of 3 to 6 capsules thus formed per day is equivalent to ingestion of nattokinase contained in 1 or 2 packs (50 to 100 g) of natto on the market.

When an enteric capsule (including an acid-resistant coat) is formed for example, 36.7 mg of Bacillus natto culture extract powder (20000 FU/g), 10 mg of soybean lecithin, 133.3 mg of soybean oil, 15 mg of beewax, and 15 mg of glycerin fatty acid ester are mixed and emulsified to obtain 210 mg in total of an emulsified mixture, and then the emulsified mixture is filled into a film cell made of 130 mg in total of a material composed 100 mg of gelatin and 30 mg of glycerin. Consequently, a soft capsule having a total weight of 340 mg is formed. This capsule thus formed is coated with 30 mg of zein to form an enteric capsule having a total weight of 370 mg. Administration of 3 to 6 capsules thus formed per day is equivalent to ingestion of nattokinase contained in 1 or 2 packs (50 to 100 g) of natto on the market.

The above described methods can also be applied to tablets, drinkable preparations, granules, pastes or the like.

Example 1

Experimental Method:

For a normal healthy subject, male: 1, to whom 6 soft capsules according to the above described Processing Example (potency of nattokinase corresponding to 2 packs of natto, 100 g) were administered, a platelet aggregation activity was measured by collecting his blood before the administration, and 2 hours, 4 hours, 6 hours, and 8 hours after the administration. Each blood sampling was performed from a brachial median vein via a 21G needle, using a tube containing 3.8% sodium citrate. An amount of the blood collected by single sampling was 11 ml, and thus 55 ml of blood was collected in total. Although this male subject did not need to be fasted, a lapse of 2 or more hours after the breakfast was required because of the nature of this examination, for the purpose of getting knowledge of the platelet aggregation activity in a certain condition similar to an actual administration condition. Each blood specimen thus obtained was subjected to centrifugation for 10 minutes at 180×g and the obtained supernatant was used as platelet rich plasma (PRP). The remaining specimen was subjected to centrifugation for 15 minutes at 1600×g and used as platelet poor plasma (PPP). The PRP was diluted with the PPP to prepare a specimen which contains platelet at a concentration of $25\pm3\times10^4/\mu l$. As an aggregation inducer, collagen [MC Medical Inc.] and ADP [MC Medical Inc.] were used. In this case, final concentrations of the collagen were 1 µg/ml and 2 µg/ml, and a final concentration of the ADP was 2 µM.

For measurement of the platelet aggregation activity, a particle measurement type of platelet aggregation activity measuring apparatus [PA-20: Kowa Co, Ltd.] employing laser scattered light was used. The apparatus PA-20 was developed on the principle that an intensity of scattered light which is generated by a beam of light impinging on a fine particle increases in proportion to a square of the particle size, and further, this apparatus can compute a platelet aggregation rate as well as a size of the produced platelet aggregate and the number thereof. In the conventional extinction method, the absorbance was lowered only after the aggregates comprising thousands of platelets were produced. However, the apparatus of the present invention can measure even small aggregates composed of tens of platelets, that is, this apparatus is excellent in its detection sensitivity. The platelet aggregate sizes were classified into three groups as follows, depending on the scattered light intensities: 25 mV<a small aggregate (particle size, 9 to 25 µm)<200 mV, 200 mV<a medium aggregate (particle size, 25 to 50 µm)<600 mV, and 600 mV<a large aggregate (particle size, 50 to 70 µm)<2,047 mV [Hoshi K., Zhou X., Terazono M., Satou Y., Yamazaki M., Miyake F., Jpn. J. Clin. Pharmacol. Ther., 32, 223–230 (2001)].

Platelet inhibition rates were calculated from an equation as follows:

Platelet inhibition rate $(\%)=(1-X/Y)\times 100$.

X: scattering intensity or OD obtained by adding ADP or collagen after ingesting nattokinase Y: scattering intensity or OD obtained by adding ADP or collagen before ingesting nattokinase.

Experimental Result:

When 1.0 µg/ml of collagen was added as a coagulant, a strong inhibitory action was observed after a lapse of 4 hours from the ingestion (FIG. 1). The platelet aggregates were reduced to their minimum sizes after 8 hours, and the inhibitory action of nattokinase on the platelets were observed (Table 1A, 1B, and 1C described below).

TABLE 1A

| Platelet aggregate | Collagen 1.0 µg/ml | | | | |
| --- | --- | --- | --- | --- | --- |
|  | 0 h | 2 h | 4 h | 6 h | 8 h |
| Large (50–70 µm) | 12 | 6 | 1 | 1 | 0 |
| Medium (25–50 µm) | 25 | 20 | 12 | 4 | 3 |
| Small (9–25 µm) | 63 | 75 | 88 | 95 | 97 |

TABLE 1B

| Platelet aggregate | Collagen 2.0 µg/ml | | | | |
|---|---|---|---|---|---|
|  | 0 h | 2 h | 4 h | 6 h | 8 h |
| Large (50–70 µm) | 31 | 35 | 31 | 27 | 25 |
| Medium (25–50 µm) | 30 | 25 | 26 | 28 | 27 |
| Small (9–25 µm) | 39 | 40 | 43 | 45 | 48 |

TABLE 1C

| Platelet aggregate | ADP 2.0 µM | | | | |
|---|---|---|---|---|---|
|  | 0 h | 2 h | 4 h | 6 h | 8 h |
| Large (50–70 µm) | 41 | 33 | 42 | 35 | 20 |
| Medium (25–50 µm) | 23 | 30 | 26 | 27 | 31 |
| Small (9–25 µm) | 36 | 37 | 33 | 37 | 49 |

Example 2

Experimental Method:

For a normal healthy subject, male: 1, to whom 6 soft capsules according to the above described Processing Example (potency of nattokinase corresponding to 2 packs of natto, 100 g) were administered, a platelet aggregation activity was measured by collecting his blood before the administration, and 2 hours, 4 hours, 6 hours, and 8 hours after the administration. Each blood sampling was performed from a brachial median vein via a 21G needle, using a tube containing 3.8% sodium citrate. An amount of the blood collected by single sampling was 11 ml, and thus 55 ml of blood was collected in total. Although this male subject did not need to be fasted, a lapse of 2 or more hours after the breakfast was required because of the nature of this examination, for the purpose of getting knowledge of the platelet aggregation activity in a certain condition similar to an actual administration condition. Each blood specimen thus obtained was subjected to centrifugation for 10 minutes at 180×g, and the obtained supernatant was used as platelet rich plasma (PRP). The remaining specimen was subjected to centrifugation for 15 minutes at 1600×g and used as platelet poor plasma (PPP). The PRP was diluted with the PPP to prepare a specimen which contains platelet at a concentration of $25\pm3\times10^4/\mu l$. As an aggregation inducer, collagen [MC Medical Inc.] and ADP [MC Medical Inc.] were used. In this case, a final concentration of the collagen was 2 µg/ml, and final concentrations of the ADP were 2 µM and 5 µM.

For measurement of the platelet aggregation activity, a particle measurement type of platelet aggregation activity measuring apparatus [PA-20: Kowa Co, Ltd.] employing laser scattered light was used. The apparatus PA-20 was developed on the principle that an intensity of scattered light which is generated by a beam of light impinging on a fine particle increases in proportion to a square of the particle size, and further, this apparatus can compute a platelet aggregation rate as well as a size of the produced platelet aggregate and the number thereof. In the conventional extinction method, the absorbance was lowered only after the aggregates comprising thousands of platelets were produced. However, the apparatus of the present invention can measure even small aggregates composed of tens of platelets, that is, this apparatus is excellent in its detection sensitivity. The platelet aggregate sizes were classified into three groups as follows, depending on the scattered light intensities: 25 mV<a small aggregate (particle size, 9 to 25 µm)<200 mV, 200 mV<a medium aggregate (particle size, 25 to 50 µm)<600 mV, and 600 mV<a large aggregate (particle size, 50 to 70 µm)<2,047 mV [Hoshi K., Zhou X., Terazono M., Satou Y., Yamazaki M., Miyake F., Jpn. J. Clin. Pharmacol. Ther., 32, 223–230 (2001)].

Platelet inhibition rates were calculated from an equation as follows:

Platelet inhibition rate $(\%) = (-X/Y) \times 100$.

X: scattering intensity or OD obtained by adding ADP or collagen after ingesting nattokinase.

Y: scattering intensity or OD obtained by adding ADP or collagen before ingesting nattokinase.

Figure 2:
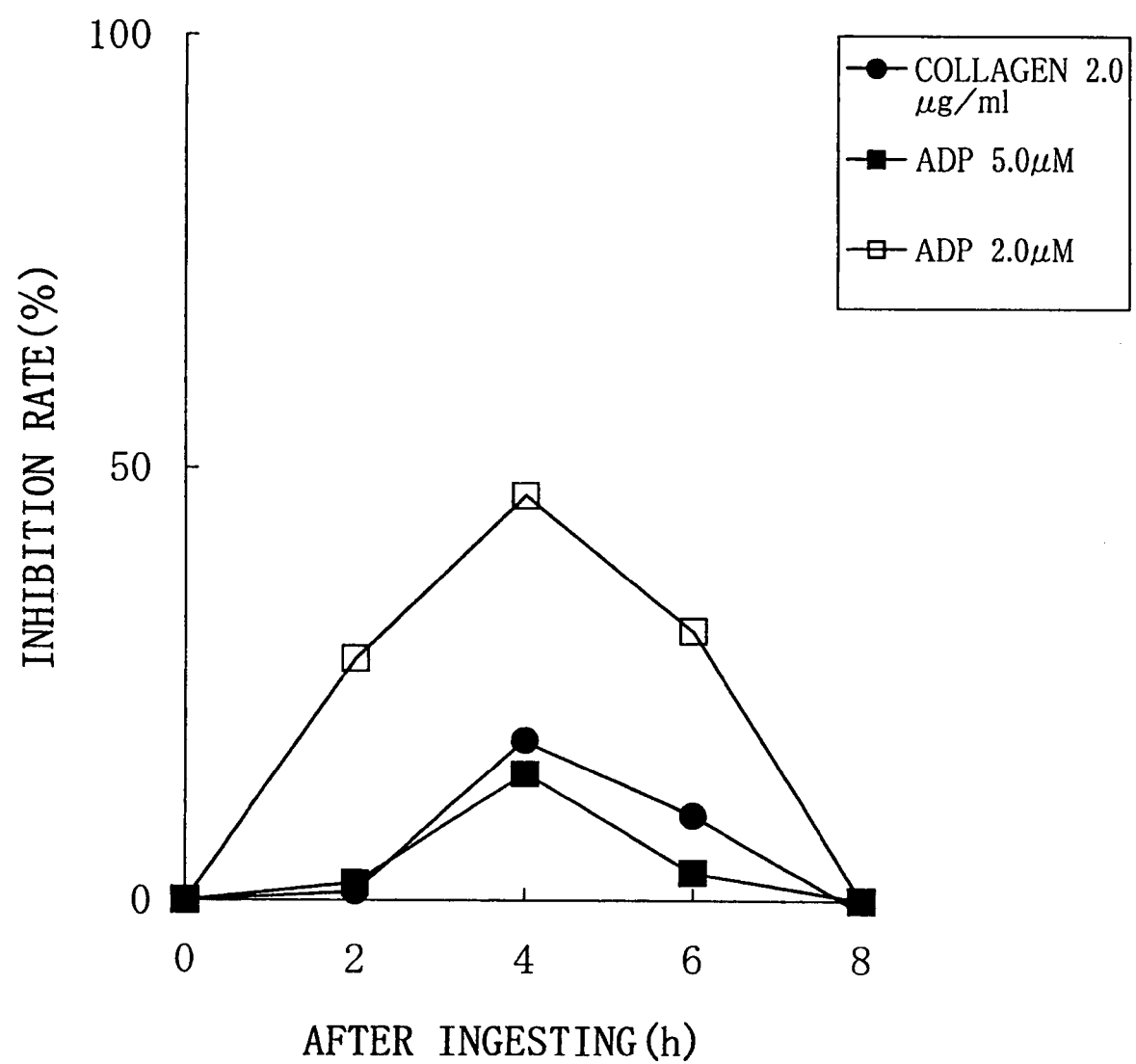
FIG. 2 is a diagram showing a change of a platelet inhibition rate with respect to time after the ingestion of nattokinase, when using collagen and ADP as inducers whose concentrations are different from those shown in FIG. 1.

Experimental Result:

When 1.0 µg/ml of collagen was added as a coagulant, a strong inhibitory action was observed after a lapse of 4 hours from the ingestion (FIG. 2).

Example 3

Experimental Method:

For a normal healthy subject, female: 1, to whom 6 soft capsules according to the above described Processing Example (potency of nattokinase corresponding to 2 packs of natto, 100 g) were administered, a platelet aggregation activity was measured by collecting her blood before the administration, and 2 hours, 4 hours, 6 hours, and 8 hours after the administration. Each blood sampling was performed from a brachial median vein via a 21G needle, using a tube containing 3.8% sodium citrate. An amount of the blood collected by single sampling was 11 ml, and thus 55 ml of blood was collected in total. Although this female subject did not need to be fasted, a lapse of 2 or more hours after the breakfast was required because of the nature of this examination, for the purpose of getting knowledge of the platelet aggregation activity in a certain condition similar to an actual administration condition. Each blood specimen thus obtained was subjected to centrifugation for 10 minutes at 180×g, and the obtained supernatant was used as platelet rich plasma (PRP). The remaining specimen was subjected to centrifugation for 15 minutes at 1600×g and used as platelet poor plasma (PPP). The PRP was diluted with the PPP to prepare a specimen which contains platelet at a concentration of $25\pm3\times10^4/\mu l$. As an aggregation inducer, collagen [MC Medical Inc.] and ADP [MC Medical Inc.] were used. In this case, final concentrations of the collagen were 1 µg/ml and 2 µg/ml, and final concentrations of the ADP were 2 µM and 5 µM.

For measurement of the platelet aggregation activity, a particle measurement type of platelet aggregation activity measuring apparatus [PA-20: Kowa Co, Ltd.] employing laser scattered light was used. The apparatus PA-20 was developed on the principle that an intensity of scattered light which is generated by a beam of light impinging on a fine particle increases in proportion to a square of the particle size, and further, this apparatus can compute a platelet aggregation rate as well as a size of the produced platelet aggregate and the number thereof. In the conventional extinction method, the absorbance was lowered only after the aggregates comprising thousands of platelets were produced. However, the apparatus of the present invention can measure even small aggregates composed of tens of platelets, that is, this apparatus is excellent in its detection sensitivity. The platelet aggregate sizes were classified into three groups as follows, depending on the scattered light intensities: 25 mV<a small aggregate (particle size, 9 to 25 μm)<200 mV, 200 mV<a medium aggregate (particle size, 25 to 50 μm)<600 mV, and 600 mV<a large aggregate (particle size, 50 to 70 μm)<2,047 mV [Hoshi K., Zhou X., Terazono M., Satou Y., Yamazaki M., Miyake F., Jpn. J. Clin. Pharmacol. Ther., 32, 223–230 (2001)].

Platelet inhibition rates were calculated from an equation as follows:

Platelet inhibition rate (%)=(1−X/Y)×100.

X: scattering intensity or OD obtained by adding ADP or collagen after ingesting nattokinase.

Y: scattering intensity or OD obtained by adding ADP or collagen before ingesting nattokinase.

Figure 3:
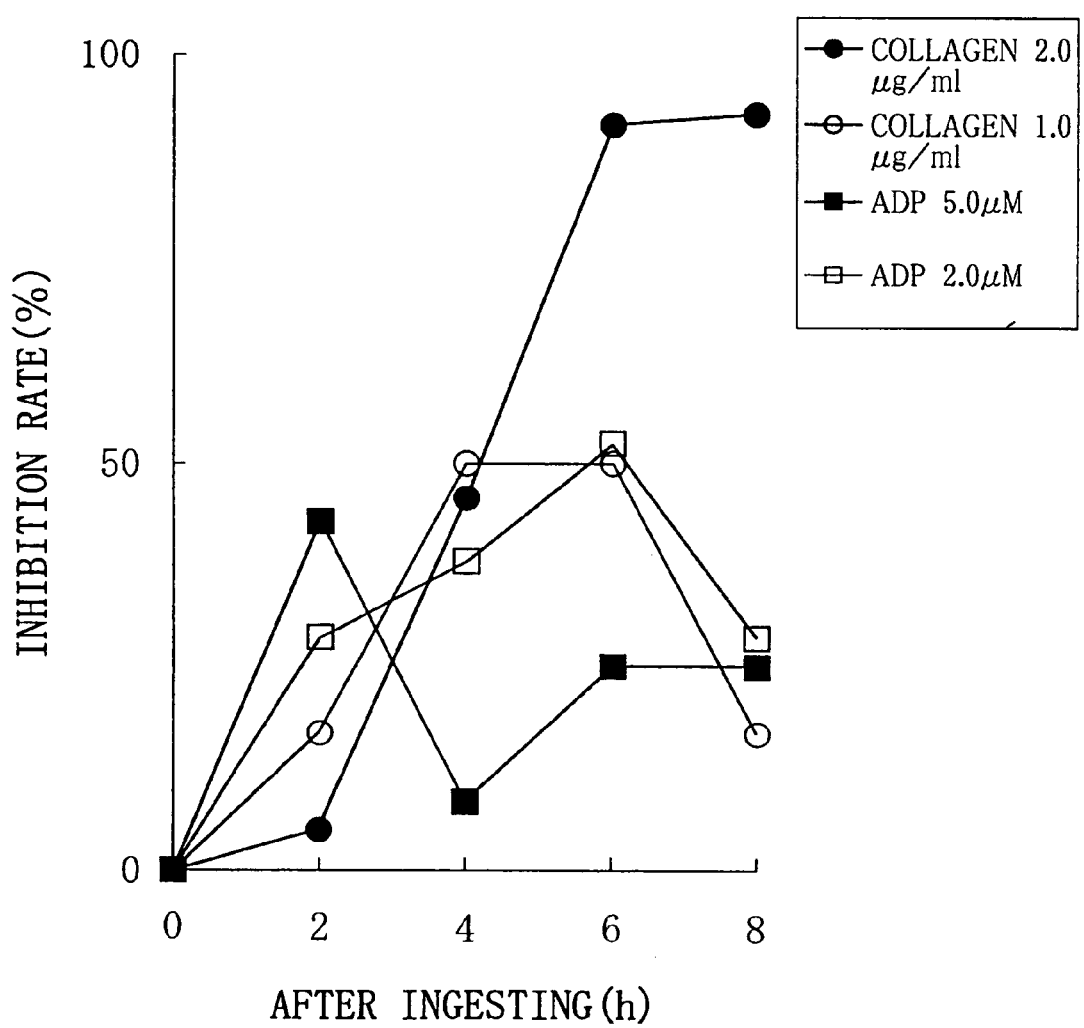
FIG. 3 is a diagram showing a change of a platelet inhibition rate with respect to time after the ingestion of nattokinase, when using collagen and ADP as inducers whose concentrations are different from those shown in FIG. 1 and FIG. 2.

Experimental Result:

When 1.0 μg/ml of collagen was added as a coagulant, a strong inhibitory action was observed after a lapse of 4 hours from the ingestion (FIG. 3). The platelet aggregates were reduced to their minimum sizes after 8 hours, and the inhibitory action of nattokinase on the platelets were observed (Table 2A and 2B described below).

TABLE 2A

| Platelet aggregate | Collagen 1.0 μg/ml | | | | |
| --- | --- | --- | --- | --- | --- |
| | 0 h | 2 h | 4 h | 6 h | 8 h |
| Large (50–70 μm) | 15 | 9 | 15 | 17 | 7 |
| Medium (25–50 μm) | 9 | 10 | 6 | 10 | 8 |
| Small (9–25 μm) | 76 | 81 | 79 | 73 | 86 |

TABLE 2B

| Platelet aggregate | Collagen 2.0 μg/ml | | | | |
| --- | --- | --- | --- | --- | --- |
| | 0 h | 2 h | 4 h | 6 h | 8 h |
| Large (50–70 μm) | 42 | 48 | 18 | 2 | 8 |
| Medium (25–50 μm) | 27 | 26 | 28 | 2 | 4 |
| Small (9–25 μm) | 32 | 26 | 55 | 96 | 88 |

Example 4

Experimental Method:

For a normal healthy subject, male: 1, to whom 6 nattokinase enteric capsules according to the above described Processing Example (potency of nattokinase corresponding to 2 packs of natto, 100 g) were administered, a platelet aggregation activity was measured by collecting his blood before the administration, and 2 hours, 4 hours, 6 hours and 8 hours after the administration. Each blood sampling was performed from a brachial median vein via a 21G needle, using a tube containing 3.8% sodium citrate. An amount of the blood collected by single sampling was 11 ml, and thus 55 ml of blood was collected in total. Although this male subject did not need to be fasted, a lapse of 2 or more hours after the breakfast was required because of the nature of this examination, for the purpose of getting knowledge of the platelet aggregation activity in a certain condition similar to an actual administration condition. Each blood specimen thus obtained was subjected to centrifugation for 10 minutes at 180×g, and the obtained supernatant was used as platelet rich plasma (PRP). The remaining specimen was subjected to centrifugation for 15 minutes at 1600×g and used as platelet poor plasma (PPP). The PRP was diluted with the PPP to prepare a specimen which contains platelet at a concentration of $25\pm3\times10^4/\mu l$. As an aggregation inducer, collagen [MC Medical Inc.] and ADP [MC Medical Inc.] were used. In this case, final concentrations of the collagen were 0.5 μg/ml, 1 μg/ml, and 2 μg/ml, and a final concentration of the ADP was 2 μM.

For measurement of the platelet aggregation activity, a particle measurement type of platelet aggregation activity measuring apparatus [PA-20: Kowa Co, Ltd.] employing laser scattered light was used. The apparatus PA-20 was developed on the principle that an intensity of scattered light which is generated by a beam of light impinging on a fine particle increases in proportion to a square of the particle size, and further, this apparatus can compute a platelet aggregation rate as well as a size of the produced platelet aggregate and the number thereof. In the conventional extinction method, the absorbance was lowered only after the aggregates comprising thousands of platelets were produced. However, the apparatus of the present invention can measure even small aggregates composed of tens of platelets, that is, this apparatus is excellent in its detection sensitivity. The platelet aggregate sizes were classified into three groups as follows, depending on the scattered light intensities: 25 mV<a small aggregate (particle size, 9 to 25 μm)<200 mV, 200 mV<a medium aggregate (particle size, 25 to 50 μm)<600 mV, and 600 mV<a large aggregate (particle size, 50 to 70 μm)<2,047 mV [Hoshi K., Zhou X., Terazono M., Satou Y., Yamazaki M., Miyake F., Jpn. J. Clin. Pharmacol. Ther., 32, 223–230 (2001)].

Platelet inhibition rates were calculated from an equation as follows:

Platelet inhibition rate (%)=(1−X/Y)×100.

X: scattering intensity or OD obtained by adding ADP or collagen after ingesting nattokinase.

Y: scattering intensity or OD obtained by adding ADP or collagen before ingesting nattokinase.

Figure 4:
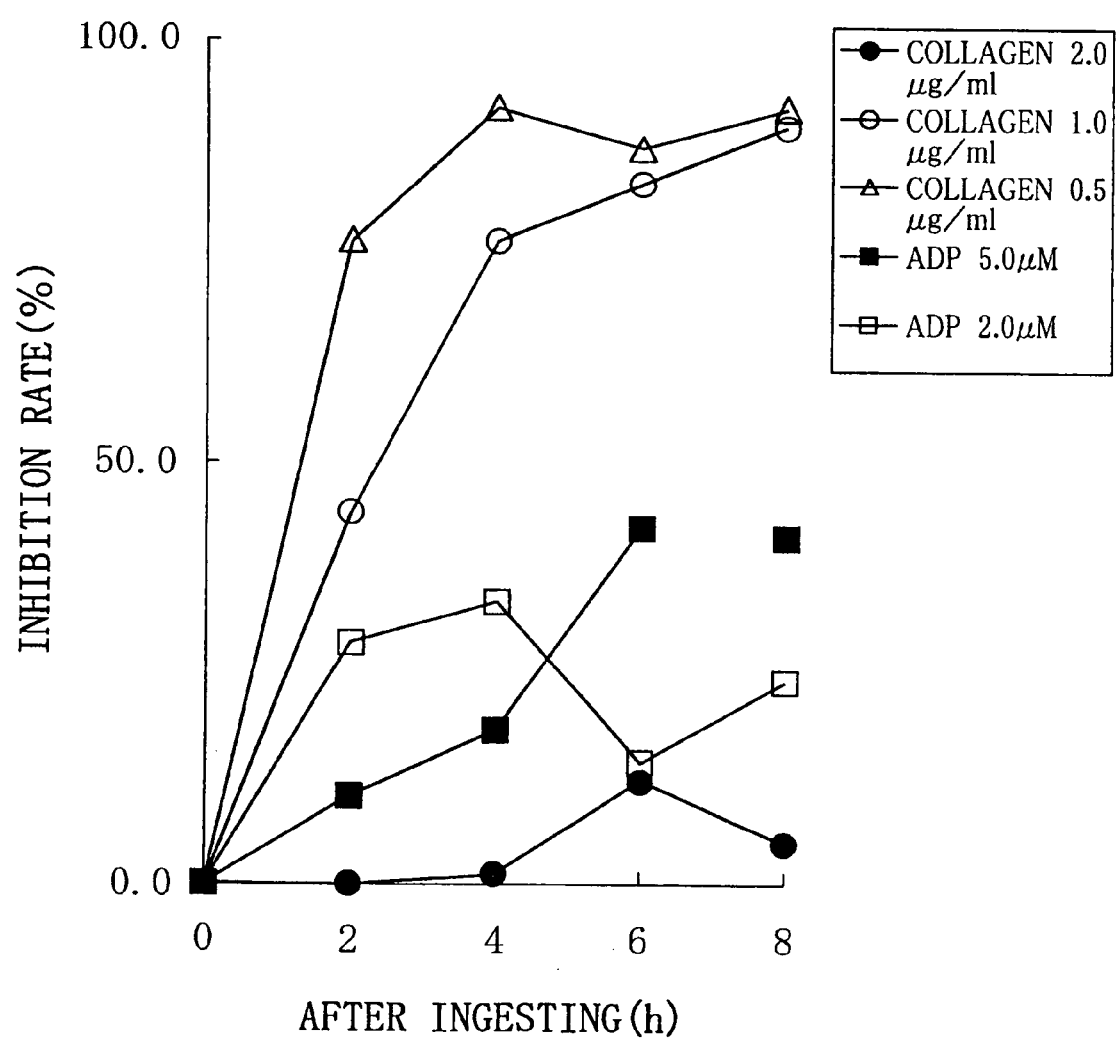
FIG. 4 is a diagram showing a change of a platelet inhibition rate with respect to time after the ingestion of nattokinase, when using collagen and ADP as inducers whose concentrations are different from those shown in FIGS. 1, 2, and 3.

Experimental Result:

When 1.0 μg/ml of collagen was added as a coagulant, a strong inhibitory action was observed after a lapse of 4 hours from the ingestion (FIG. 4). The platelet aggregates were reduced to their minimum sizes after 8 hours, and the inhibitory action of nattokinase on the platelets were observed (Table 3A and 3B described below).

TABLE 3A

| Platelet aggregate | Collagen 0.5 μg/ml | | | | |
| --- | --- | --- | --- | --- | --- |
| | 0 h | 2 h | 4 h | 6 h | 8 h |
| Large (50–70 μm) | 31 | 8 | 6 | 6 | 1 |
| Medium (25–50 μm) | 23 | 6 | 2 | 3 | 1 |

TABLE 3A-continued

| | Collagen 0.5 μg/ml | | | | |
|---|---|---|---|---|---|
| Platelet aggregate | 0 h | 2 h | 4 h | 6 h | 8 h |
| Small (9–25 μm) | 47 | 85 | 93 | 91 | 99 |

TABLE 3B

| | Collagen 1.0 μg/ml | | | | |
|---|---|---|---|---|---|
| Platelet aggregate | 0 h | 2 h | 4 h | 6 h | 8 h |
| Large (50–70 μm) | 37 | 11 | 2 | 3 | 5 |
| Medium (25–50 μm) | 22 | 21 | 14 | 2 | 3 |
| Small (9–25 μm) | 41 | 68 | 84 | 95 | 93 |

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

What is claimed is:

1. A process for inhibiting platelet aggregation in a subject in need of treatment to inhibit platelet aggregation, comprising:
    administering to the subject a composition whose active ingredient is nattokinase containing 1 μg/g or less of vitamin $K_2$ on a dry weight basis.

2. A process of claim 1, wherein the composition is a supplement food.

3. A process for treating myocardial infarction in a subject in need of treatment to prevent myocardial infarction, comprising:
    administering to the subject a platelet aggregation inhibitor whose active ingredient is nattokinase containing 1 μg/g or less of vitamin $K_2$ on a dry weight basis.

4. The process of claim 3, wherein the composition is a supplement food.

5. A process for treating brain infarction in a subject in need of treatment to prevent brain infarction, comprising:
    administering to the subject a platelet aggregation inhibitor whose active ingredient is nattokinase containing 1 μg/g or less of vitamin $K_2$ on a dry weight basis.

6. The process of claim 5, wherein the composition is a supplement food.

* * * * *